United States Patent [19]

Sholder

[11] Patent Number: 5,190,034

[45] Date of Patent: Mar. 2, 1993

[54] IMPLANTABLE ARRHYTHMIA SYSTEM WITH PROTECTION AGAINST RELEASE OF UNNEEDED PULSES

[75] Inventor: Jason A. Sholder, Northridge, Calif.

[73] Assignee: Siemens Pacesetter, Inc., Sylmar, Calif.

[21] Appl. No.: 639,642

[22] Filed: Jan. 10, 1991

[51] Int. Cl.[5] ............................................. A61N 1/362
[52] U.S. Cl. ............................................. 128/419 PG
[58] Field of Search ...... 128/419 D, 419 PG, 419 PT

[56] References Cited

U.S. PATENT DOCUMENTS

| | | | |
|---|---|---|---|
| 3,534,282 | 10/1970 | Day | 330/149 |
| 4,063,410 | 12/1977 | Welling | 58/38 R |
| 4,086,916 | 5/1978 | Freeman et al. | 128/2.05 T |
| 4,088,139 | 5/1978 | Auerbach | 128/419 PT |
| 4,102,346 | 7/1978 | Fulker | 128/419 PS |
| 4,105,023 | 8/1978 | Marchese et al. | 128/2.06 B |
| 4,114,628 | 9/1978 | Rizk | 128/419 PG |
| 4,345,603 | 8/1982 | Schulman | 128/419 PT |
| 4,376,992 | 3/1983 | Aizawa | 368/47 |
| 4,407,289 | 10/1983 | Nappholz et al. | 128/419 PG |
| 4,576,170 | 3/1986 | Bradley et al. | 128/419 D |
| 4,595,009 | 6/1986 | Leinders | 128/419 D |
| 4,979,506 | 12/1990 | Silvian | 128/419 PG |
| 5,044,365 | 9/1991 | Webb et al. | 128/419 PG |
| 5,076,272 | 12/1991 | Ferek-Petric | 128/419 PG |

FOREIGN PATENT DOCUMENTS 1101238  10/1982  U.S.S.R. ......................... 128/419 PG

OTHER PUBLICATIONS

Kim et al., "Automatic Implantable Cardioverter/Defibrillator: Inadvertent Discharges During Permanent Pacemaker Magnet Tests, " *PACE*, vol. 10 (May–Jun. 1987, Part I), pp. 579–582.

Primary Examiner—William E. Kamm
Assistant Examiner—George Manuel
Attorney, Agent, or Firm—Leslie S. Miller; Lisa P. Weinberg; Malcolm J. Romano

[57] ABSTRACT

An implantable arrhythmia treatment system includes a sensor which generates an electrical signal corresponding to a physiological characteristic of a patient, the physiological characteristics and thus the electrical signal exhibit a change given the onset of an arrhythmia. The electrical signal is supplied to a fibrillation detector in an implantable housing, which initiates an appropriate treatment sequence upon the detection of the onset of the arrhythmia. Simultaneously with initiating the treatment sequence, the fibrillation detector causes, either by direct connection or by telemetry communication, the generation of an alarm signal which informs the patient that the sequence has been initiated, so that the patient knows that a treatment pulse is about to be released. The implantable unit includes circuitry responsive to a signal externally generated by the patient which prevents the release of the defibrillating pulse. If the patient feels no need for such a pulse, i.e. if the onset of the arrhythmia has been erroneously detected, the patient can thereby prevent the release of the pulse.

34 Claims, 4 Drawing Sheets

IMPLANTABLE ARRHYTHMIA SYSTEM WITH PROTECTION AGAINST RELEASE OF UNNEEDED PULSES

BACKGROUND OF THE INVENTION

1. Field of the Invention

The present invention is directed to implantable defibrillator systems, and in particular to such systems which include means for permitting communication between components of the implanted system and external, control signal-generating elements.

2. Description of the Prior Art

Implantable defibrillation systems are known in the art which deliver a high-voltage defibrillation pulse to the heart when the onset of fibrillation is detected and/or in the event of a detected complete loss of cardiac output. Such known devices are also capable, if the heart exhibits an arrhythmia such as atrial fibrillation, atrial flutter or tachycardia, or ventricular tachycardia, of cardioverting the heart by delivering a low-voltage pulse in an attempt to regain synchronous operation of the heart, instead of delivering the high voltage defibrillation pulse. In known devices of this type, considerable effort has been devoted to the development of detection circuitry to accurately identify heart arrhythmias which require defibrillation or cardioversion (i.e., insuring true-positives) and for preventing a "no output" situation when an output is actually needed (i.e., preventing true-negatives). In conventional systems of this type, however, adequate steps have not been taken to prevent the delivery of a defibrillation or cardioversion pulse when none is needed (i.e., preventing false-positives).

It is important to provide a safety mechanism for preventing implantable systems of this type from releasing a treatment pulse when the patient feels no need for such a pulse. A false-positive output could result in severe discomfort to the patient, and may trigger ventricular tachycardia, ventricular fibrillation and ultimately death if the system cannot react quickly enough to provide proper treatment to revive the patient.

It is known from U.S. Pat. No. 4,086,916 to contain a cardiac monitoring system in a wristwatch worn by a patient, the system including circuitry for detecting an erratic heartbeat, a missing pulse or other irregularities and providing an alarm indication, audio and visual, when such an event is detected.

It is also known from U.S. Pat. No. 4,088,139 to provide, in an implantable cardiac pacing system, means for generating a marking pulse in the pacemaker monitoring system if an event such as loss of capture occurs. The patient is not immediately informed of the occurrence of such an event, however, the system is provided with telemetry means so that when the recorded data is subsequently read out and examined by a physician, the data will include the marker indicating that loss of capture has occurred. The physician can then take such corrective steps as may be necessary.

An implantable pacing system is disclosed in U.S. Pat. No. 4,102,346 which includes an alarm device as part of the implanted unit which generates an alarm signal to inform the pacemaker user when the battery source of power of the pacemaker is nearing end of life or is malfunctioning.

An implantable tissue stimulating device is disclosed in U.S. Pat. No. 4,345,603 which activates an alarm which informs the patient in whom the system is implanted that the battery is in need of replacement. After the user has been so informed, the user applies a magnet externally in the vicinity of the implanted unit to deactivate the monitoring system and thereby cease the continued operation of the alarm.

A pacemaker for controlling tachycardia is disclosed in U.S. Pat. No. 4,407,289 also disclosing means for informing a pacemaker user of the remaining battery life. The user places a magnet externally in the vicinity of the implanted unit, which thereby causes the implanted unit to generate two pulses, which can be seen on the patient's ECG waveform. The time separation between the two pulses indicates the remaining battery potential. Application of the magnet, after the pulses have been generated, temporarily disables the device.

SUMMARY OF THE INVENTION

It is an object of the present invention to provide an implantable arrhythmia treatment system which includes reliable protection against the release of unneeded treatment pulses, i.e., which provides protection against a false-positive output.

It is a further object of the present invention to provide such a device which is user-interactive so that the prevention of the release of a pulse when the patient feels no need of such a pulse can be prevented directly by the patient in whom the system is implanted.

The above and other objects are achieved in accordance with the principles of the present invention in an arrhythmia treatment system which has a sensor implantable in a patient which senses a physiological characteristic which exhibits a change upon the onset of a cardiac arrhythmia and which generates an electrical signal corresponding to the sensed physiological characteristic. The electrical signal is supplied to implanted circuitry which monitors the signal and, upon the detection of a change in the signal indicative of the onset of an arrhythmia, initiates an appropriate treatment sequence, which includes the generation and release of at least one defibrillation pulse or cardioversion pulse. Simultaneously with the initiation of the treatment sequence, an alarm is generated which informs the patient in whom the system is implanted that such a treatment sequence has been initiated, and that a treatment pulse will therefore be released shortly. The implanted system includes means responsive to an externally-generated signal from the patient for stopping the release of the treatment pulse, so that if the patient feels no need for such a pulse the patient can optionally prevent its release. Thus, if the system has mistakenly identified the presence of an arrhythmia, at a time when no arrhythmia in fact exists, the patient will be informed of this fact and can take steps to prevent the release of a treatment pulse, thereby avoiding the discomfort and potential danger of such a pulse.

The alarm generator may be disposed in the implanted unit, or in an external unit. The alarm may be of any type which does not require constant, active monitoring by the user, such as a sensory alarm, such as an audio alarm generator or a tactile alarm generator ("tickler").

In one embodiment, the alarm generator is contained in the implanted unit, and the implanted unit also includes circuitry responsive to the presence of a magnetic field which prevents the release of the treatment pulse by ceasing charging of the capacitance which is used to generate the pulse. The magnetic field is applied by the patient by bringing a magnet in the vicinity of the implanted unit. In another embodiment with the alarm generator contained within in the implanted unit, the implanted unit contains a telemetry receiver. The patient is provided with an external control unit, which includes a telemetry transmitter. Upon perceiving the alarm, the user actuates a control element on the external device, which causes the generation and telemetry transmission of an inhibit signal. The inhibit signal which is received by the implanted unit is then supplied to logic circuitry which causes charging of the capacitance to cease.

In a further embodiment, wherein the alarm generator is disposed in an external unit, the initiation of an arrhythmia treatment sequence causes the telemetry transmission of a signal via a telemetry transmitter in the implanted unit. The external unit has a telemetry receiver which, upon receipt of the signal, activates the alarm. In one version of this embodiment, the telemetry system provides for two-way communication, so that the patient can actuate a control element on the external unit to generate an inhibit instruction, which is then transmitted telemetrically to the implanted unit, which then ceases the charging of the capacitance. In another version of this embodiment, the user applies a magnet in the vicinity of the implanted unit, and magnetically responsive means in the implanted unit are thereby actuated, which cause charging of the capacitance to cease.

DESCRIPTION OF THE PREFERRED EMBODIMENTS

Figure 1:
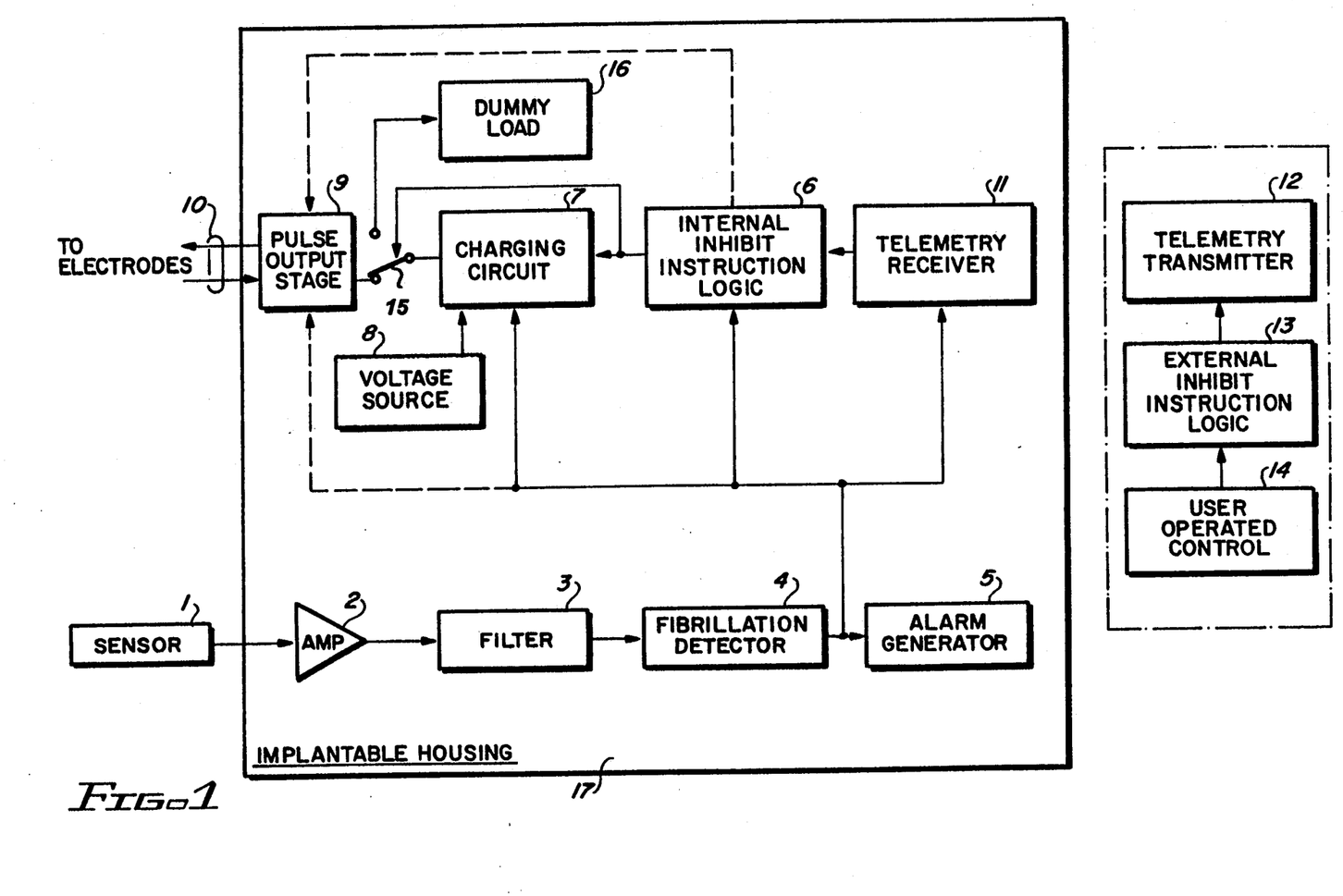
FIG. 1 is a schematic block diagram of a first embodiment of an arrhythmia treatment system constructed in accordance with the principles of the present invention.

As shown in FIG. 1 an arrhythmia treatment system constructed in accordance with the principles of the present invention includes implanted components, to the left of the vertical dashed line representing a patient's skin, and external components, to the right of the vertical dashed line. The implanted components include a sensor 1 of the type known to those skilled in the art which senses a physiological characteristic of a patient which exhibits a change upon the onset of a cardiac arrhythmia such as ventricular fibrillation or a complete loss of cardiac output, which require therapy in the form of a high-voltage defibrillation pulse, and arrhythmias such as atrial fibrillation, atrial flutter or tachycardia, or ventricular tachycardia, which call for treatment in the form of a low-voltage cardioversion pulse. The sensor generates an electrical signal corresponding to the sensed physiological characteristic, this signal being supplied to the input of an amplifier 2 via an in vivo electrical connection. The amplifier 2 is one of a number of components contained within an implantable housing 17. The output of the amplifier 2 is supplied to a filter 3 which filters the amplified sensor output in a known manner and which supplies the filtered result to the input of a fibrillation detector 4. The fibrillation detector 4 is a known circuit which is capable of analyzing the amplified, filtered sensor output to detect the presence of signal components or combinations of components which indicate the onset of one of the above-described types of cardiac arrhythmia. Upon the detection of the onset of cardiac arrhythmia, the fibrillation detector 4 generates an output signal which, in the embodiment of FIG. 1, is supplied to an alarm generator 5, also contained in the implantable housing 17, as well as to internal inhibit instruction logic 6 and to a telemetry receiver 11. In the embodiment of FIG. 1, the output of the fibrillation detector 4 is supplied to the internal inhibit instruction logic 6 and the telemetry receiver 11 only to temporarily enable those units, so that those units need not be constantly supplied with power. The output of the fibrillation detector 4 is also supplied to a charging circuit 7, which initiates the charging of a capacitance therein from a voltage source 8. (It will be understood that the other components within the implantable housing 17 are connected to, and receive power from, the voltage source 8 as well, but those standard connections have been omitted for clarity.) The output of the charging circuit 7 is supplied via a switch 15 to a pulse output stage 9. The pulse output stage 9 is connected to leads 10 which respectively terminate in standard defibrillation/cardioversion pulse delivery and return electrodes. When the voltage at the output of the charging circuit 7 reaches a predetermined level, as sensed by the pulse output stage 9, the pulse output stage 9 releases a treatment pulse calculated to provide therapy for the type of arrhythmia which has been detected. It is also possible for the pulse output stage 9 simply to release a pulse after a predetermined time following initiation of charging within the charging circuit 7. This alternative is shown by the dashed line connection from the output of the fibrillation detector 4 to the pulse output stage 9. The release of a treatment pulse can therefore be controlled by sensing the voltage level within the charging circuit 7, or simply as a function of time, or both. Under any alternative, however, there will be a time delay of a number of seconds between the initiation of charging and the release of a pulse.

This time delay is sufficient to permit the user in whom the system has been implanted to take steps to prevent the release of the treatment pulse, if the user feels no need for such treatment. In the embodiment of FIG. 1, the user having been informed by the alarm generator 5 that a treatment sequence has been initiated, the user can actuate a user operated control 14 which causes the generation of an inhibit instruction in external inhibit instruction logic 13. This inhibit instruction is supplied to a telemetry transmitter 12, which transmits the inhibit instruction telemetrically to the implanted telemetry receiver 11. The telemetry transmitter 12, the external inhibit instruction logic 13 and the user operated control 14 in combination form an external unit which may be contained in a commonly worn item, such as a wristwatch.

The telemetry receiver and the telemetry transmitter 12 have, in the embodiment of FIG. 1 been so designated because those units need only individually perform the functions of receiving and transmitting within the context of the embodiment of FIG. 1. Apart from the functions related to the invention disclosed herein, however, there may be a need for additional communication between the implanted components and the external components, in which case each of the units 11 and 12 will be a transceiver.

Upon receipt of the inhibit instruction, the telemetry receiver 11 supplies a signal to the internal inhibit instruction logic 6, which in turn supplies a signal to the charging circuit 7 which immediately causes charging of the capacitance to cease. As long as this occurs before the predetermined voltage level has been reached on the capacitance, and/or before the elapse of a predetermined time, this will prevent the release of the treatment pulse. As further insurance against the release of such a pulse, the internal inhibit instruction logic 6 may supply a disenable signal to the pulse output stage 9, as indicated by the dashed line connection between those components.

Since receipt of an inhibit instruction will leave the capacitance in the charging circuit 7 partially charged, means must be provided to permit draining or discharge of this voltage. For this purpose, the output of the internal inhibit instruction logic 6 is used to switch the switch 15, so that the output of the charging circuit 7 is supplied to a dummy load 16. Discharge of the capacitance within the charging circuit 7 can thus take place into the dummy load 16.

It will be understood that although the sensor 1 has been schematically shown as being separate from the leads 10 in FIG. 1, the sensor 1 can be incorporated in those leads in a manner known to those skilled in the art.

In the other embodiments of FIGS. 2, 3 and 4, components identical to those already discussed in connection with FIG. 1 have been provided with the same reference numerals and, unless otherwise stated, perform the same function as described in connection with the embodiment of FIG. 1.

Figure 2:
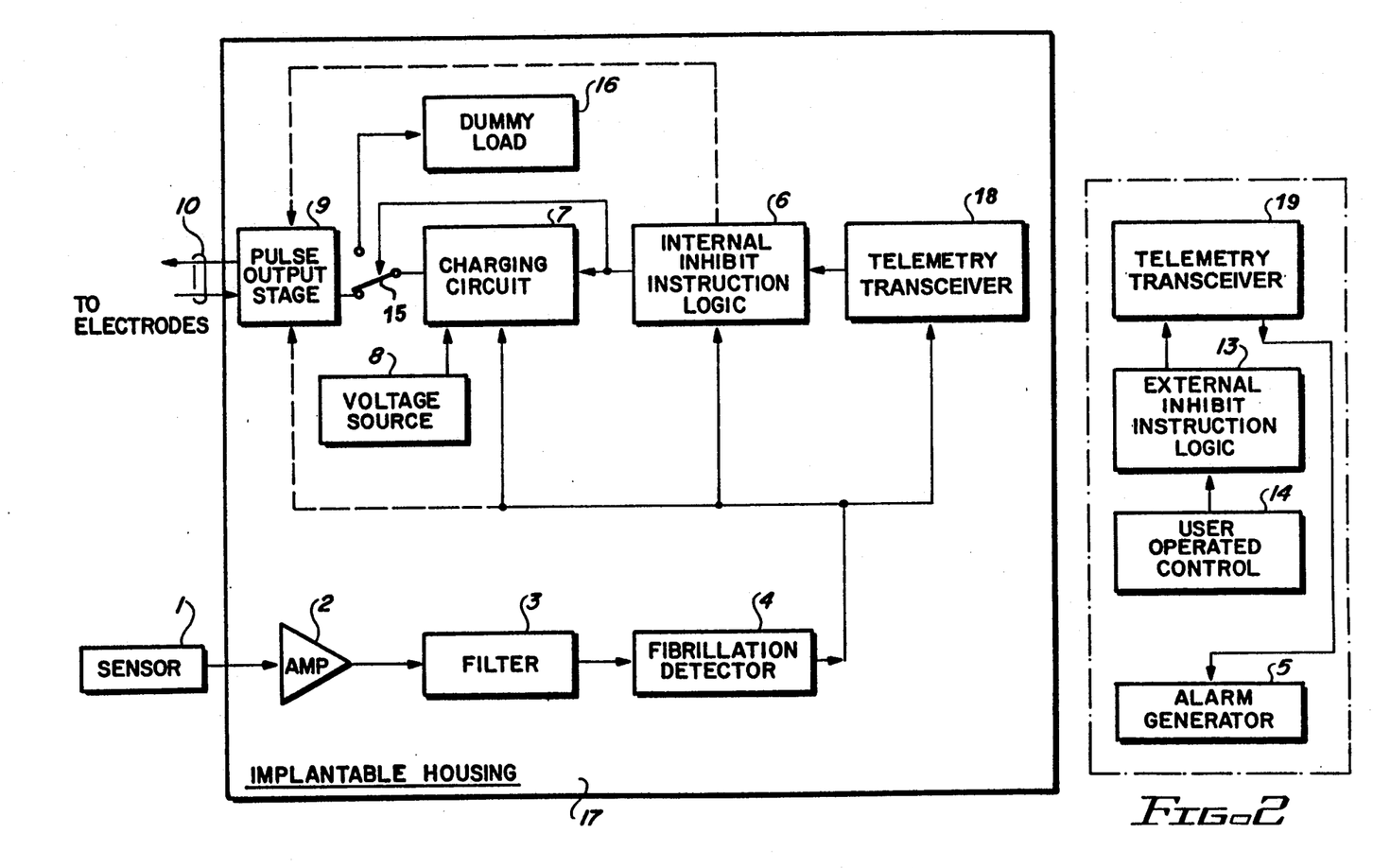
FIG. 2 is a schematic block diagram of a second embodiment of an arrhythmia treatment system constructed in accordance with the principles of the present invention.

In the embodiment of FIG. 2, the alarm generator 5 is disposed externally. In this embodiment, the output of the fibrillation detector 4 is supplied to a elemetry transceiver 18 in the implantable housing 17. The telemetry transceiver 18 thereupon transmits a signal telemetrically to a telemetry transceiver 19. Upon receipt of this signal, the telemetry transceiver 19 supplies a signal to the alarm generator 5, which causes the alarm to be generated. The user can then take the same steps as discussed in connection with the embodiment of FIGURE by entering an inhibit instruction via the user operated control 14, which is then telemetrically transmitted from the telemetry receiver 19 to the telemetry transceiver 18. The reaction of the components within the implantable housing 17 to the receipt of this inhibit instruction is the same as described above in connection with the embodiment of FIG. 1. Again, the external components can be easily accommodated in a commonly worn item, such as a wristwatch.

Figure 3:
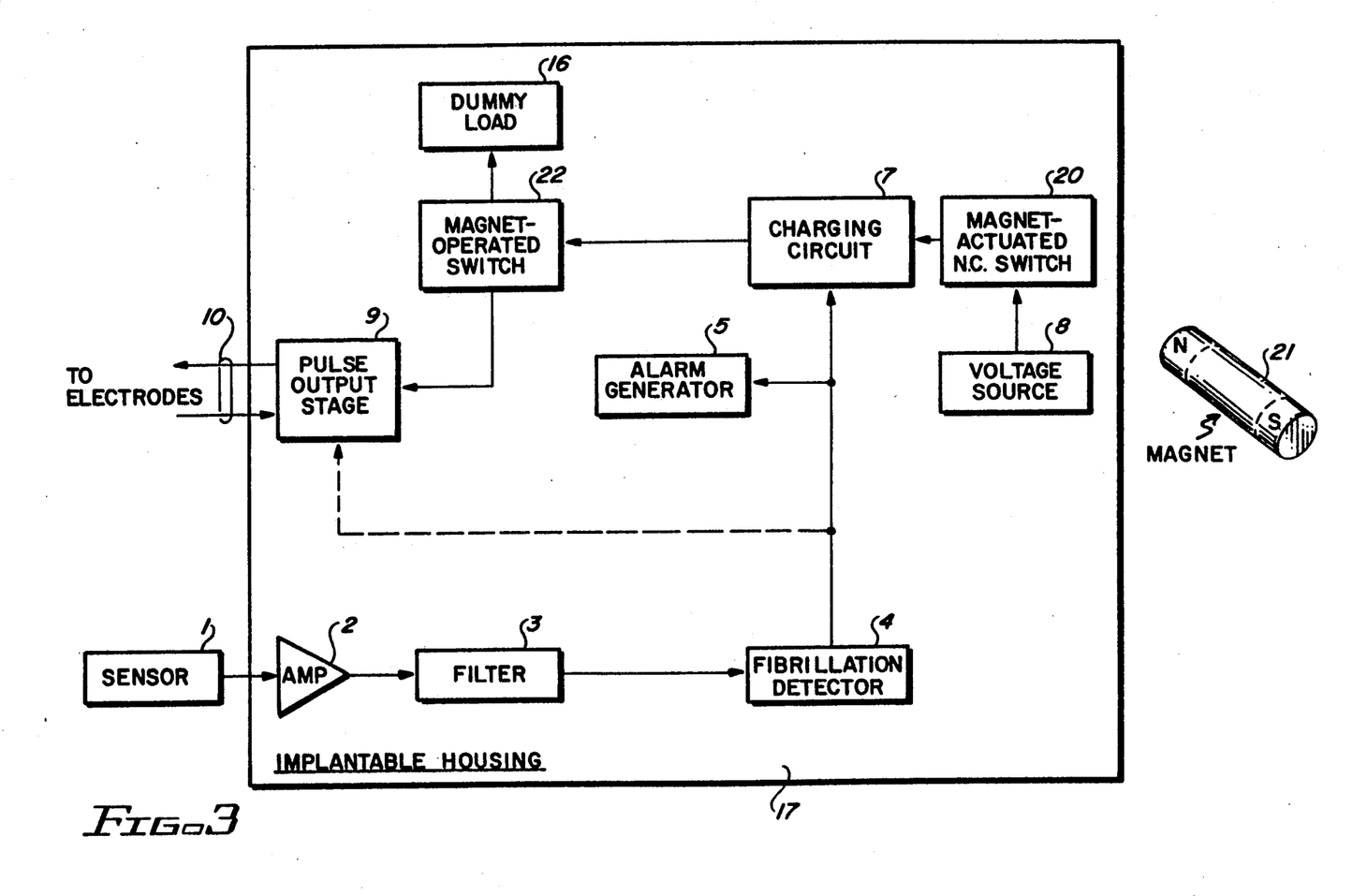
FIG. 3 is a schematic block diagram of a third embodiment of an arrhythmia treatment system constructed in accordance with the principles of the present invention.

An embodiment which avoids the use of telemetry components is disclosed in FIG. 3. In this embodiment, the output of the fibrillation detector 4 is supplied only to the alarm generator 5 and the carging circuit 7 (and possibly to the pulse output stage 9). The charging circuit 7 is connected to the voltage source 8 through a magnet actuated normally closed switch 20. Since the switch 20 is normally closed, charging of the capacitance in the charging circuit 7 will be immediately initiated, as in the above embodiments. If the patient, upon being informed of the initiation of a treatment sequence by the alarm generator 5, does not feel the need for a treatment pulse, the patient brings a magnet 21 in the vicinity of the implantable housing 17, causing the normally closed switch 20 to open, thereby ceasing charging of the capacitance in the carging circuit 7. In place of the switch 15 at the output of the charging circuit 7, the embodiment of FIG. 3 employs a magnet operated switch 22. Simultaneously with the opening of the switch 20, the magnetic field generated by the magnetic 21 causes the switch 22 to switch so that the output of the charging circuit is supplied to the dummy load 16, thereby permitting discharge of the capacitance.

Figure 4:
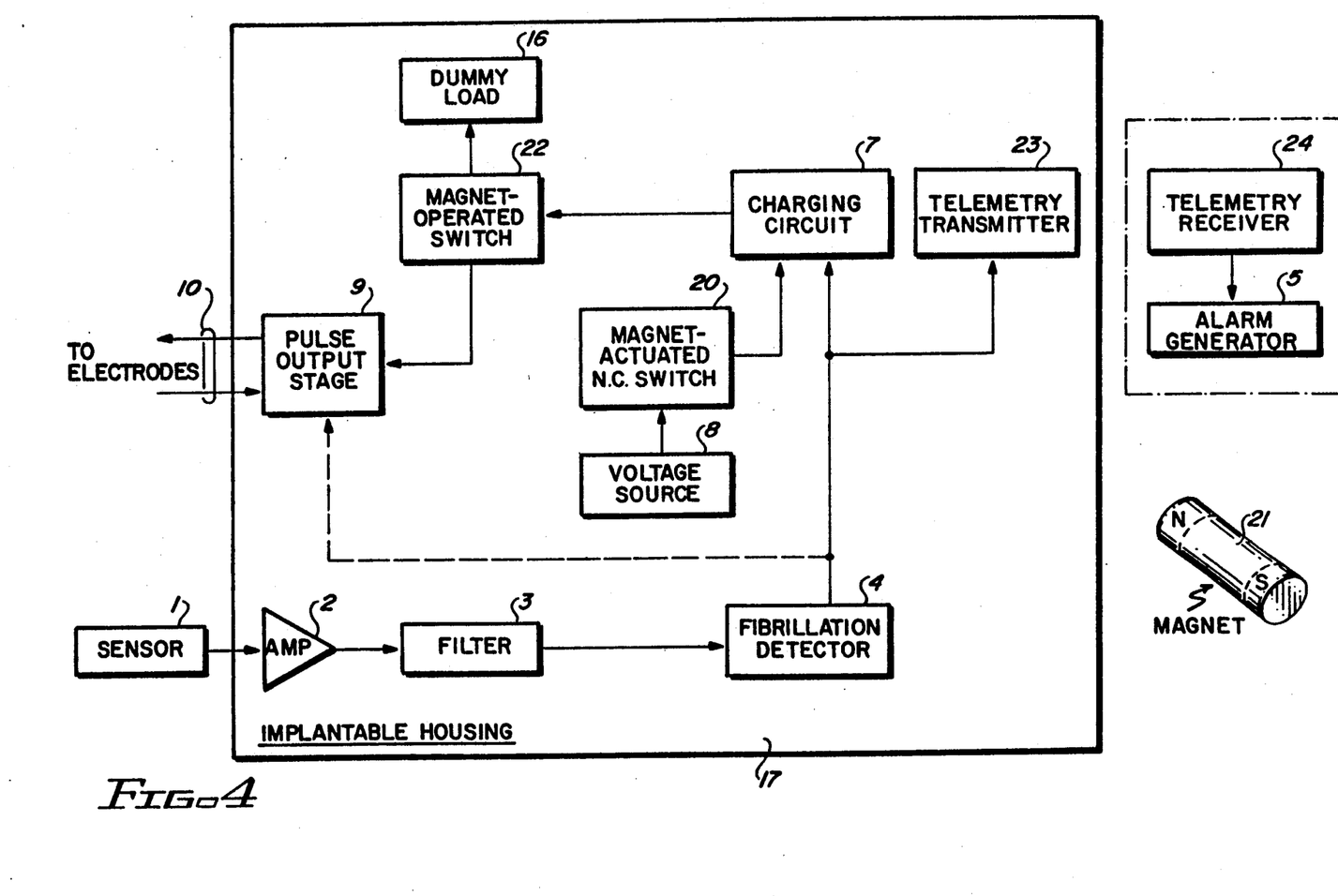
FIG. 4 is a schematic block diagram of a fourth embodiment of an arrhythmia treatment system constructed in accordance with the principles of the present invention.

The embodiment of FIG. 4 uses a combination of telemetry and magnetic-responsive components. In this embodiment, the output of the fibrillation detector 4 is supplied to a telemetry transmitter 23 in the implantable housing 17. The telemetry transmitter 23 in the implantable housing 17. The telemetry transmitter 23 transmits a signal to the external telemetry receiver 24. Upon receipt of the signal the telemetry receiver 24 supplies a signal to the alarm generator 5, thereby informing the user that a treatment sequence has been initiated. If desired, the user can then apply the magnet 21, as in the embodiment of FIG. 3, to actuate the normally closed switch 20 and the switch 22, thereby preventing release of the treatment pulse.

Although modifications and changes may be suggested by those skilled in the art, it is the intention of the inventor to embody within the patent warranted hereon all changes and modifications as reasonably and properly come within the scope of his contribution to the art.

What is claimed is:

1. An arrhythmia treatment system comprising: sensor means adapted for implantation in a patient for sensing a physiological characteristic which exhibits a change upon the onset of cardiac arrhythmia and for generating an electrical signal corresponding to said physical characteristic;

treatment means contained in a housing adapted for implantation in a patient, said treatment means adapted to be connected in vivo to said sensor means to receive said electrical signal therefrom for initiating an arrhythmia treatment sequence, including releasing a treatment pulse in vivo to said patient via electrodes adapted for implantation in said patient, in response to said change in said physical characteristic;

means in communication with said treatment means for informing said patient, substantially simultaneously with the initiation of said arrhythmia treatment sequence, that said arrhythmia treatment sequence has been initiated; and means in communication with said treatment means and operable by said patient for optionally stopping said arrhythmia treatment sequence before releasing said treatment pulse.

2. An arrhythmia treatment system, as claimed in claim 1, wherein said means for informing said patient that said arrhythmia treatment sequence has been initiated includes a sensory alarm.

3. An arrhythmia treatment system, as claimed in claim 2, wherein said sensory alarm is disposed externally of said patient.

4. An arrhythmia treatment system, as claimed in claim 3, wherein said means for informing said patient that said arrhythmia treatment sequence has been initiated further includes telemetry transmitter means disposed in said housing for transmitting a telemetry signal in response to said change in said physical characteristic and telemetry receiver means disposed externally of said patient for receiving said signal from said telemetry transmitter means and for actuating said sensor alarm.

5. An arrhythmia treatment system, as claimed in claim 4, wherein said means operable by said patient for optionally stopping said arrhythmia treatment sequence includes means in said housing for stopping said arrhythmia treatment sequence in the presence of a magnetic field, and a magnet manipulably by said patient to place said magnetically responsive means in the presence of a magnetic field generated by said magnet.

6. An arrhythmia treatment system, as claimed in claim 5, wherein said treatment means includes a voltage source and means for charging a capacitance from said voltage source in response to said change in said physical characteristic to generate said treatment pulse, and wherein said magnetically responsive means includes a magnetically actuated normally closed switch connected between said voltage source and said means for charging which switches to an open state in the presence of said magnetic field.

7. An arrhythmia treatment system, as claimed in claim 6, further comprising a dummy load contained in said housing, and wherein said magnetically responsive means includes a magnetically actuated switch means connected to an output of said means for charging, to said electrodes and to said dummy lead for normally connecting said output to said electrodes and switchable to permit discharge of said capacitance into said dummy load in the presence of said magnetic field.

8. An arrhythmia treatment system, as claimed in claim 3, wherein said means for informing said patient that said arrhythmia treatment sequence has been initiated further includes first telemetry transceiver means disposed in said housing for transmitting a telemetry signal in response to said change in said physical characteristic, and for receiving externally generated telemetry signals, and second telemetry transceiver means disposed externally of said patient for receiving said signal from said first telemetry transceiver means and for actuating said sensor alarm, and for generating external telemetry signals.

9. An arrhythmia treatment system, as claimed in claim 8, wherein said means operable by said patient for optionally stopping said arrhythmia treatment sequence includes means in said housing for stopping said arrhythmia sequence upon the telemetric receipt of an inhibit instruction, and logic means, connected to said second telemetry transceiver means, operable by said patient for generating said inhibit instructions, said inhibit instruction being telemetrically transmitted from said second telemetry transceiver means to said first telemetry transceiver means and thereby stopping said arrhythmia treatment sequence.

10. An arrhythmia treatment system, as claimed in claim 9, wherein said treatment means includes a voltage source and means for charging a capacitance from said voltage source in response to said change in said physical characteristic to generate said treatment pulse, and wherein said means responsive to said inhibit instruction is a means for ceasing charging of said capacitance upon receipt of said inhibit instruction.

11. An arrhythmia treatment system, as claimed in claim 10, further comprising a dummy load contained in said housing, and wherein said means responsive to said inhibit instruction includes switch means connected to an output of said means for charging, to said electrodes and to said dummy load for normally connecting said output to said electrodes and switchable in response to said inhibit instruction to permit discharge of said capacitance into said dummy load.

12. An arrhythmia treatment system, as claimed in claim 2, wherein said sensory alarm is disposed in said housing.

13. An arrhythmia treatment system, as claimed in claim 12, wherein said means operable by said patient for optionally stopping said arrhythmia treatment sequence includes means in said housing for stopping said arrhythmia treatment sequence in the presence of a magnetic field, and a magnet manipulable by said patient to place said magnetically responsive means in the presence of a magnetic field generated by said magnet.

14. An arrhythmia treatment system, as claimed in claim 13, wherein said treatment means includes a voltage source and means for charging a capacitance from said voltage source in response to said change in said physical characteristic to generate said treatment pulse, and wherein said magnetically responsive means includes a magnetically actuated normally closed switch connected between said voltage source and said means for charging which switches to an open state in the presence of said magnetic field.

15. An arrhythmia treatment system, as claimed in claim 14, further comprising a dummy load contained in said housing, and wherein said magnetically responsive means includes a magnetically actuated switch means connected to an output of said means for charging, to said electrodes and to said dummy load for normally connecting said output to said electrodes and switchable to permit discharge of said capacitance into said dummy load in the presence of said magnetic field.

16. An arrhythmia treatment system, as claimed in claim 12, wherein said means operable by said patient for optionally stopping said arrhythmia treatment sequence includes telemetry receiver means disposed in said housing for receiving an externally generated inhibit instruction and first logic means disposed in said housing for stopping said arrhythmia treatment sequence upon receipt of said inhibit instruction by said telemetry receiver means, second logic means, disposed externally of said patient and operable by said patient, for generating said inhibit instruction, and telemetry transmitter means disposed externally of said patient and connected to said second logic means for telemetrically transmitting said inhibit instruction to said telemetry receiver means.

17. An arrhythmia treatment system, as claimed in claim 16, wherein said treatment means includes a voltage source and means for charging a capacitance from said voltage source in response to said change in said physical characteristic to generate said treatment pulse, and wherein said first logic means is a means for ceasing charging of said capacitance upon receipt or said inhibit instruction.

18. An arrhythmia treatment system, as claimed in claim 17, further comprising a dummy load contained in said housing and wherein said means for optionally stopping said arrhythmia treatment sequence includes a switch in said housing connected to an output of said means for charging, to said electrodes and to said dummy load for normally connecting said output to said electrodes and switchable in response to said inhibit instruction to permit discharge of said capacitance into said dummy load.

19. An arrhythmia treatment system, as claimed in claim 1, wherein said treatment means includes a voltage source and means for charging a capacitance from said voltage source in response to said change in said physical characteristic to generate said treatment pulse, and wherein said means for optionally stopping said arrhythmia treatment sequence includes means for ceasing charging of said capacitance.

20. An arrhythmia treatment system, as claimed in claim 19, further comprising a dummy load contained in said housing, and wherein said means for optionally stopping said arrhythmia treatment sequence includes switch means connected to an output of said means for charging, to said electrodes and to said dummy load for normally connecting said output to said electrodes and switchable to permit discharge of said capacitance into said dummy load if said patient stops said arrhythmia treatment sequence.

21. An arrhythmia treatment system comprising:
sensor means adapted for implantation in a patient for sensing a physiological characteristic which exhibits a change upon the onset of cardiac arrhythmia and for generating an electrical signal corresponding to said physical characteristic;
means contained in a housing adapted for implantation in a patient and adapted to be connected in vivo to said sensor means to receive said electrical signal therefrom for generating a treatment initiation signal upon the onset of cardiac arrhythmia;
a voltage source in said housing;
means in said housing for charging a capacitance from said voltage source in response to said treatment initiation signal for generating a treatment pulse;
pulse output means connected to an output of said means for charging for releasing said treatment pulse after a time following said treatment initiation signal;
alarm means connected to said means for generating said treatment initiation signal for receiving said signal therefrom for informing a patient in whom said housing is implanted that a treatment sequence has been initiated;
first logic means disposed externally of said patient and optionally operable by said patient to generate an inhibit instruction after said patient has been informed that a treatment sequence has been initiated;
telemetry transmitter means disposed externally of said patient and connected to said first logic means for telemetrically transmitting said inhibit instruction;
telemetry receiver means disposed in said housing for receiving said inhibit instruction from said telemetry transmitter means; and
second logic means disposed in said housing and connected to said telemetry receiver means and said means for charging for preventing, in response to the receipt said inhibit instruction before elapse of said time, at least one of further charging of said capacitance by said means for charging or releasing of said treatment pulse by said pulse output means.

22. An arrhythmia treatment system comprising:
sensor means adapted for implantation in a patient for sensing a physiological characteristic which exhibits a change upon the onset of cardiac arrhythmia and for generating an electrical signal corresponding to said physical characteristic;
means contained in a housing adapted for implantation in a patient and adapted to be connected in vivo to said sensor means to receive said electrical signal therefrom for generating a treatment initiation signal upon the onset of cardiac arrhythmia;
a voltage source in said housing;
means in said housing for charging a capacitance from said voltage source in response to said treatment initiation signal for generating a treatment pulse;
pulse output means connected to an output of said means for charging for releasing said treatment pulse after a time following said treatment initiation signal;
first telemetry transceiver means disposed in said housing and connected to said means for generating a treatment initiation signal for telemetrically transmitting a signal in response to said treatment initiation signal, and for receiving externally generated signals;
second telemetry transceiver means disposed externally of said patient for receiving said signal from said first telemetry transceiver means, and for transmitting signals to said first telemetry transceiver means;
alarm means disposed externally of said patient and connected to said second telemetry transceiver means for generating an alarm upon receipt of said signal from said first telemetry transceiver means for informing a patient in whom said housing is implanted that a treatment sequence has been initiated;
first logic means disposed externally of said patient and connected to said second telemetry transceiver means and optionally operable by said patient to generate an inhibit instruction after said patient has been informed that a treatment sequence has been initiated, said inhibit instruction being telemetrically transmitted from said second telemetry transceiver to said first telemetry transceiver; and
second logic means disposed in said housing and connected to said first telemetry receiver for preventing, in response to receipt of said inhibit instruction before elapse of said time, at least one of further charging of said capacitance by said means for charging or releasing of said treatment pulse by said pulse output means.

23. An arrhythmia treatment system comprising:
sensor means adapted for implantation in a patient for sensing a physiological characteristic which exhibits a change upon the onset of cardiac arrhythmia and for generating an electrical signal corresponding to said physical characteristic;
means contained in a housing adapted for implantation in a patient and adapted to be connected in vivo to said sensor means to receive said electrical signal therefrom for generating a treatment initiation signal upon the onset of cardiac arrhythmia;
a voltage source in said housing;
means in said housing for charging a capacitance from said voltage source in response to said treatment initiation signal for generating a treatment pulse;
pulse output means connected to an output of said means for charging for releasing said treatment pulse after a time following said treatment initiation signal;
alarm means connected to said means for generating said treatment initiation signal for receiving said signal therefrom for informing a patient in whom said housing is implanted that a treatment sequence has been initiated;

a magnetically actuated normally closed switch connected between said voltage source and said means for charging which switches to an open state in the presence of a magnetic field; and a magnet manipulable by said patient after said patient has been informed by said alarm means that a treatment sequence has been initiated to place said magnetically actuated normally closed switch in the presence of a magnetic field generated by said magnet thereby to open said magnetically actuated normally closed switch to cease charging of said capacitance.

24. An arrhythmia treatment system comprising:

sensor means adapted for implantation in a patient for sensing a physiological characteristic which exhibits a change upon the onset of cardiac arrhythmia and for generating an electrical signal corresponding to said physical characteristic;

means contained in a housing adapted for implantation in a patient and adapted to be connected in vivo to said sensor means to receive said electrical signal therefrom for generating a treatment initiation signal upon the onset of cardiac arrhythmia;

a voltage source in said housing;

means in said housing for charging a capacitance from said voltage source in response to said treatment initiation signal for generating a treatment pulse;

pulse output means connected to an output of said means for charging for releasing said treatment pulse after a time following said treatment initiation signal;

telemetry transmitter means disposed in said housing and connected to said means for generating a treatment initiation signal for telemetrically transmitting a signal in response to said treatment initiation signal;

telemetry receiver means disposed externally of said patient for receiving said signal from said telemetry transmitter means;

alarm means disposed externally of said patient and connected to said telemetry receiver means for informing said patient that a treatment sequence has been initiated;

a magnetically actuated normally closed switch, connected in said housing between said voltage source and said means for charging, which switches to an open state in the presence of a magnetic field; and a magnet manipulable by said patient after being informed that a treatment sequence has been initiated to optionally place said magnetically actuated normally closed switch in the presence of a magnetic field generated by said magnet to open said magnetically actuated normally closed switch to cease charging of said capacitance.

25. An arrhythmia treatment method comprising:

sensing a physiological characteristic of a patient which exhibits a change upon the onset of cardiac arrhythmia using a sensor implanted in said patient;

generating an electrical signal with said sensor corresponding to said physical characteristic;

generating, in response to said change in said physical characteristic, a signal in circuitry contained in a housing implanted in the patient which initiates an arrhythmia treatment sequence including generating and releasing a treatment pulse in vivo to said patient;

informing said patient, substantially simultaneously with the initiation of said arrhythmia treatment sequence, that said arrhythmia treatment sequence has been initiated; and said patient, after being informed of the initiation of said arrhythmia treatment sequence, optionally communicating with circuitry in said housing to stop said arrhythmia treatment sequence before the release of said treatment pulse.

26. A method, as claimed in claim 25, wherein the step of informing said patient is further defined by informing said patient that an arrhythmia treatment sequence has been initiated by activating an alarm contained within said housing.

27. A method, as claimed in claim 26, wherein the step of said patient optionally stopping said arrhythmia treatment sequence is further defined by the steps of: providing circuitry in said housing which stops said arrhythmia treatment sequence in the presence of a magnetic field; and providing said patient with a magnet manipulable by said patient to place said circuitry in said housing in the presence of a magnetic field generated by said magnet to stop said arrhythmia treatment sequence.

28. A method, as claimed in claim 26, wherein the step of said patient optionally stopping said arrhythmia treatment sequence is further defined by the steps of: said patient operating external logic circuitry to generate an inhibit instruction;

telemetrically transmitting said inhibit instruction to telemetry circuitry disposed in said housing; and stopping said arrhythmia treatment sequence in said housing upon receipt of said inhibit instruction.

29. A method, as claimed in claim 25, wherein the step of informing said patient is further defined by the step of informing said patient that an arrhythmia treatment sequence has been initiated by activating an alarm externally of said patient.

30. A method, as claimed in claim 29, comprising the additional steps of:

generating a telemetry signal in said housing simultaneously with initiating said arrhythmia treatment sequence and telemetrically transmitting said signal; and telemetrically receiving said signal externally of said patient and thereupon activating said external alarm.

31. A method, as claimed in claim 29, wherein the step of said patient optionally stopping said arrhythmia treatment sequence is further defined by the steps of: providing circuitry in said housing which stops said arrhythmia treatment sequence in the presence of a magnetic field; and providing said patient with a magnet manipulable by said patient to place said circuitry in said housing in the presence of a magnetic field generated by said magnet to stop said arrhythmia treatment sequence.

32. A method, as claimed in claim 29, wherein the step of said patient optionally stopping said arrhythmia treatment sequence is further defined by the steps of: said patient operating external logic circuitry to generate an inhibit instruction;

telemetrically transmitting said inhibit instruction to telemetry circuitry disposed in said housing; and stopping said arrhythmia treatment sequence in said housing upon receipt of said inhibit instruction.

33. An arrhythmia treatment method, as claimed in claim 25, wherein the step of generating a treatment pulse is further defined by charging a capacitance in said housing to a selected voltage and discharging said capacitance to generate said pulse.

34. A arrhythmia treatment method, as claimed in claim 33, comprising the additional steps of:
providing a dummy load in said housing; and
directing the discharge of said capacitance in said housing into said dummy load if said patient stops said arrhythmia treatment sequence.

* * * * *